United States Patent [19]

Unno et al.

[11] Patent Number: 5,721,111
[45] Date of Patent: Feb. 24, 1998

[54] METHOD FOR DETERMINATION OF UREA NITROGEN

[75] Inventors: Tomoko Unno, Gotenba; Norihito Aoyama, Sunto-gun, both of Japan

[73] Assignee: Kyowa Medex Co., Ltd., Tokyo, Japan

[21] Appl. No.: 541,176

[22] Filed: Oct. 11, 1995

[30] Foreign Application Priority Data

Oct. 13, 1994 [JP] Japan .................. 6-248053

[51] Int. Cl.⁶ .................................. C12Q 1/58
[52] U.S. Cl. ............... 435/12; 435/962; 423/282
[58] Field of Search ............. 435/12, 962; 423/282

[56] References Cited

U.S. PATENT DOCUMENTS

| | | | |
|---|---|---|---|
| 3,876,502 | 4/1975 | Monte et al. | 195/99 |
| 3,926,734 | 12/1975 | Gray et al. | 195/103.5 R |
| 4,194,063 | 3/1980 | Frank et al. | 435/12 |
| 4,282,316 | 8/1981 | Modrovich | 435/12 |
| 4,378,430 | 3/1983 | Modrovich | 435/12 |
| 4,462,819 | 7/1984 | Van Der Puy et al. | 71/28 |
| 4,732,849 | 3/1988 | Seshimoto et al. | 435/12 |

FOREIGN PATENT DOCUMENTS

| | | |
|---|---|---|
| 0054096 | 6/1982 | European Pat. Off. |
| 59-151900 | 8/1984 | Japan. |
| 3-065160 | 10/1991 | Japan. |
| 648060 | 2/1985 | Switzerland. |

OTHER PUBLICATIONS

Patent Abstracts of Japan, vol. 8, No. 283 (C–258) 25 Dec. 1984 Chem. Abs., vol. 86, No. 20 (16 May 1977) 145933S.

Nishi et al., Saishin Kensa, vol. 1, (1983) pp. 11–14.

Saishin Kensa, vol. 1, (1983) pp. 11–14.

*Primary Examiner*—Ralph Gitomer
*Attorney, Agent, or Firm*—Fitzpatrick, Cella, Harper & Scinto

[57] ABSTRACT

A method for stabilizing urease in an assay reagent for determination of urea nitrogen in a sample and a method for accurately determining urea nitrogen in a sample are disclosed. After urea nitrogen in the sample is reacted with urease in the presence of an organic boron compound, the amount of ammonia formed by the reaction is determined.

5 Claims, No Drawings

METHOD FOR DETERMINATION OF UREA NITROGEN

BACKGROUND OF THE INVENTION

1. Field of the Invention

The present invention relates to a method for the quantitative determination of urea nitrogen which is useful in clinical diagnosis.

The present invention also relates to a method for stabilizing urease and to an assay reagent composition containing stabilized urease.

2. Description of the Prior Art

Previous methods for quantitatively determining urea nitrogen in samples include methods in which urea nitrogen is acted on by urease and the amount of ammonia formed is determined by the use of indophenol or by the use of glutamate dehydrogenase ["Saishin Kensa" (Latest Examination), vol. 1, pp. 11–14, (1983)]. However, in these methods, urease used is unstable, and it is difficult to maintain the stability of the assay reagent for a long period of time.

Japanese Published Examined Patent Application No. 65160/1991 discloses a method in which boric acid that is a competitive inhibitor to urease is added to stabilize the enzyme so as to improve the quantitative determination. However, this method requires the addition of boric acid in a large amount and exhibits poor reproducibility.

Accordingly, a need exists for a better determination method for urea nitrogen.

SUMMARY OF THE INVENTION

An object of the present invention is to stabilize urease in a liquid assay reagent which is used for quantitatively determining urea nitrogen.

In accordance with the present invention, urea nitrogen in a sample can be determined by: subjecting urea nitrogen to reaction utilizing the action of urease in the presence of an organic boron compound; and then determining the amount of ammonia formed.

DETAILED DESCRIPTION OF THE INVENTION

According to the present invention, the activity of urease can be stabilized by the use of an organic boron compound.

Examples of the organic boron compound used in the present invention include trialkyl borate such as trimethyl borate and triethyl borate; triaryl borate such as triphenyl borate; trialkanolamine borate such as triethanolamine borate; triarylamine borate; and tri-o-tolyl borate. Of these, triethanolamine borate, triphenyl borate and tri-o-tolyl borate are preferable. These compounds may be used alone or in combination.

In the present invention, any urease which is classified under Enzyme No. E.C. 3.5.1.5 can be used. Examples of urease include urease derived from plants such as sword bean, urease derived from microorganisms such as bacteria (for example, *Bacillus pasteurii*), yeasts and fungi, and urease derived from animals. Urease derived from microorganisms is preferable. Urease modified by genetic engineering or the like, may also be used.

In order to stabilize urease, the organic boron compound is added in an amount of $1\times10^{-10}$ to 1 mol/U (international unit) of urease, preferably $1\times10^{-8}$ to $1\times10^{-1}$ mol/U.

The present invention also provides an assay reagent composition for quantitatively determining urea nitrogen.

The assay reagent composition comprises urease and a stabilizing amount of the organic boron compound.

The assay reagent composition may be in the form of either a liquid or a lyophilized preparation. The lyophilized assay reagent composition is dissolved in an aqueous medium immediately prior to use.

Examples of the aqueous medium include purified water, physiological saline and buffers. The buffers are preferably used. Examples of the buffer agent used in the buffer include hydrochloric acid, phosphoric acid, carbonic acid, phthalic acid, tris, oxalic acid, ethylenediamine tetraacetic acid (EDTA), maleic acid, glycine, pyrophosphoric acid, malonic acid, fumaric acid, DL-tartaric acid, citric acid, furancarboxylic acid, β-alanine, β:β'-dimethylglutaric acid, DL-lactic acid, γ-aminoleutyric acid, barbituric acid, benzoic acid, succinic acid, ε-aminocaproic acid, acetic acid, propionic acid, DL-malic acid, 5(4)-hydroxyimidazole, glycerol phosphoric acid, β-glycerophosphoric acid or salts thereof, ethylenediamine, imidazole, 5(4)-methylimidazole, N-ethylmorpholine, 5,5-diethylbarbituric acid, 2,5(4)-dimethylimidazole, 2-amino-2-methyl-1,3-propanediol, 2-amino-2-ethyl-1,3-propanediol, diethanolamine, 4-aminopyridine, ethanolamine, ephedrine, 2-amino-2-hydroxymethyl-1,3-propanediol (HEPPSO), 2-amino-2-methyl-1-propanol, n-butylamine, triethylamine, hexamethylenediamine, piperidine and Good's buffer. These buffer agents may be used either singly or in combination. Examples of the preferable buffer include tris-hydrochloride buffer, triethanolamine buffer and HEPPSO buffer. The buffer agent is used at a concentration of 0.005 to 2 mol/l. The buffer is adjusted to pH 6 to 10, preferably 7 to 9.

The assay reagent composition contains urease at a concentration of 1 to 100 U/ml, preferably 5 to 45 U/ml, and the organic boron compound at a concentration of 0.01 to 100 mM, preferably 0.01 to 5 mM.

The assay reagent composition may further contain other enzymes, coenzymes, chromogenic agents, surfactants, cheleting agents, other stabilizers and other substances.

Examples of other enzymes include glutamate dehydrogenase [E.C. 1.4.1.2, E.C. 1.4.1.3 and E.C. 1.4.1.4].

Examples of the coenzymes include reduced nicotinamide adenine dinucleotide (NADH) and reduced nicotinamide adenine dinucleotide phosphate (NADPH).

Examples of the chromogenic agents include those used for Berthelot-indophenol reaction such as a combination of phenol and sodium hypochlorite and a combination of salicylate and dichloroisocyanurate.

Surfactants such as polyethylene glycol mono-p-isooctylphenyl ether, cheleting agents such as ethylenediaminetetraacetic acid, other stabilizers such as boric acid and other substances such as α-ketoglutaric acid (α-KG) may be used.

The present invention is effective in any case where urea nitrogen in a sample is quantitatively determined by the use of urease.

In the method of the present invention, urea nitrogen in a sample is subjected to reaction with urease in the presence of the organic boron compound, usually in the aqueous medium. The concentration of the organic boron compound in the reaction mixture is 0.01 to 100 mM, preferably 0.01 to 5 mM.

After the reaction using urease, the amount of ammonia formed is determined.

The determination of ammonia may be carried out by known methods, for example, by a method using indophenol and a method using glutamate dehydrogenase ["Saishin Kensa" (Latest Examination), vol. 1, pp. 11-14, (1983)]. In the latter method, the ammonia formed is reacted with glutamate dehydrogenase in the presence of α-KG, and NADH or NADPH, and the amount of ammonia is determined by measuring the enzyme activity.

More specifically, ammonia and α-KG as substrates are reacted with glutamate dehydrogenase derived from bacteria, fungi or animals [E.C. 1.4.1.3 or E.C. 1.4.1.4] in the presence of a coenzyme NADH or NADPH, and the amount of NADH or NADPH decreased is determined by spectrophotofluorometry or visible ultraviolet spectrophotometry, whereby the amount of ammonia is determined and then the amount of the corresponding urea nitrogen is determined.

The method of the present invention is applicable to any sample that contains urea nitrogen. For example, the method can be effectively applied to fluids which are collected from a living body, such as blood, serum, urine, cerebrospinal fluid, peritoneal fluid and dialyzate.

Examples of the aqueous medium include purified water, physiological saline and buffers. The buffers are preferably used. The same buffer agents as mentioned above can be used. The pH of the buffer used in the enzyme reaction is 7 to 10, preferably 7.5 to 9.5, ideally 8.5 to 9.5. When the buffer is used to store glutamate dehydrogenase, the pH of the buffer is 8 to 10, preferably 9 to 10. When the buffer is used to store urease, the pH of the buffer is 7 to 10, preferably 8 to 9.

Determination of urea nitrogen according to the present invention is described in detail below.

(1) Method using indophenol:

To a buffer adjusted to pH 7 to 10, preferably 7.5 to 9.5, are added 1 to 100 U/ml, preferably 5 to 45 U/ml urease, 0.01 to 100 mM, preferably 0.01 to 5 mM organic boron compound, and 0.1 to 50 mM, preferably 1 to 20 mM α-KG. The mixture is preincubated at a buffer temperature of 10° to 50° C., preferably 20° to 40° C. for 3 to 5 minutes. Subsequently, a sample is added thereto, and the resulting mixture is subjected to reaction at 10° to 50° C., preferably 20° to 40° C. for 3 to 60 minutes, preferably 5 to 30 minutes. After the completion of reaction, the amount of ammonia in the reaction mixture is determined using indophenol, and the amount of the corresponding urea nitrogen is determined.

(2) Method using glutamate dehydrogenase:

In order to eliminate ammonia in a sample, the sample is added to the first reagent prepared by adding 1 to 1,000 U/ml, preferably 5 to 50 U/ml glutamate dehydrogenase, 1 to 50 mM, preferably 1 to 20 mM NADH or NADPH, and 0.1 to 50 mM, preferably 1 to 20 mM α-KG to a buffer adjusted to pH 8 to 10, preferably 9 to 10, followed by preincubation at a buffer temperature of 10° to 50° C., preferably 20° to 40° C. for 3 to 5 minutes.

Separately, 1 to 100 U/ml, preferably 5 to 45 U/ml urease, 0.01 to 100 mM, preferably 0.01 to 5 mM organic boron compound, and optionally 0.1 to 50 mM, preferably 1 to 20 mM α-KG are added to a buffer adjusted to pH 7 to 10, preferably 8 to 9 to prepare the second reagent. The second reagent is preincubated, if necessary, at a buffer temperature of 10° to 50° C., preferably 20° to 40° C. for 1 to 10 minutes.

The second reagent is added to the first reagent containing the sample so that the pH of the mixture becomes 7.5 to 9.5, preferably 8.5 to 9.5, and the mixture is subjected to reaction at 10° to 50° C., preferably 20° to 40° C. for 3 to 60 minutes, preferably 5 to 30 minutes. The ratio of the second reagent to the first reagent in the mixture is 1:9 to 9:1, preferably 1:3. Ammonia formed by the urease reaction is converted to glutamic acid by the glutamate dehydrogenase reaction. The amount of NADH or NADPH decreased by the glutamate dehydrogenase reaction per unit time is determined by spectrophotofluorometry or visible ultraviolet spectrophotometry, whereby the amount of the corresponding urea nitrogen in the sample is determined.

A solubilizing agent for the sample may be added to the buffer used in the above-mentioned process. Examples of the solubilizing agent include surfactants such as HS-210 (trademark for a product of Nippon Oils and Fats Co., Ltd.), PGM-50 (trademark for a product of Wako Pure Chemical Industries, Ltd.), Triton X-100 (trademark for a product of Sigma Co.), DF-16 (trademark for a product of Sigma Co.), Emulgen A-60 (trademark for a product of Kao Soap Co., Ltd.), Emulgen A-90 (trademark for a product of Kao Soap Co., Ltd.), and Emulgen 709 (trademark for a product of Kao Soap Co., Ltd.); inorganic salts such as sodium chloride and potassium chloride; and sodium EDTA.

Certain embodiments of the present invention are illustrated in the following examples.

EXAMPLE 1

Determination of urea nitrogen in a standard serum:

TABLE 1

| | | |
|---|---|---|
| First reagent | Tris-hydrochloride buffer (pH 9.2) | 100 mM |
| | α-KG | 1 mg/ml |
| | NADPH | 0.3 mg/ml |
| | Glutamate dehydrogenase | 20 U/ml |
| Second reagent | Tris-hydrochloride buffer (pH 8.5) | 100 mM |
| | α-KG | 4 mg/ml |
| | Triethanolamine borate | 0.01–2.5 mM |
| | Urease | 9 U/ml |

The first reagent was prepared by dissolving α-KG, NADPH and GLDH in 100 ml of 100 mM tris-hydrochloride buffer (pH 9.2) to give the concentrations shown in Table 1. The second reagent was prepared by dissolving α-KG, trieethanolamine borate (Nakarai Chemicals, Ltd.), and urease (derived from a microorganism of the genus Corynebacterium) in 100 ml of 100 mM tris-hydrochloride buffer (pH 8.5) to give the concentrations shown in Table 1. A mixture of 2.25 ml of the first reagent and 30 µl of a standard serum was preincubated at 37° C. for 5 minutes. Then, 0.75 ml of the second reagent preincubated beforehand at 37° C. for 5 minutes was added thereto. The mixture was subjected to reaction at 37° C. for 5 minutes. By measuring the decrease in the absorbance of the mixture at 340 nm per unit time, the amount of urea nitrogen in the standard serum was determined. The above procedure was repeated 20 times to calculate the coefficient of variation for within-assay (CV).

For comparison, determination of urea nitrogen in the standard serum was carried out 20 times according to the same procedure as described above except that boric acid was used instead of triethanolamine borate in the second reagent to calculate the CV.

Further, as a control experiment, determination of urea nitrogen in the standard serum was carried out 20 times according to the same procedure as described above except that triethanolamine borate was excluded from the composition of the second reagent to calculate the CV.

The results are shown in Table 2.

TABLE 2

| Concentration of additive (mM) | CV (%) | |
|---|---|---|
| | boric acid | triethanolamine borate |
| 0.01 | 1.8 | 1.4 |
| 0.05 | 2.0 | 1.1 |
| 0.10 | 2.2 | 1.5 |
| 0.20 | 2.6 | 1.3 |
| 0.40 | 2.1 | 1.5 |
| 0.80 | 1.9 | 1.5 |
| 1.60 | 2.4 | 2.0 |
| 2.50 | 2.6 | 1.6 |
| 0.00 (control group) | | 1.6 |

Table 2 reveals that the group containing the organic boron compound exhibits a lower CV than the group containing boric acid at each concentration and the use of the organic boron compound remarkably improves the determination method for urea nitrogen in accuracy.

EXAMPLE 2

Stabilization of urease activity:

The second reagent (0.75 ml) having the composition shown in Table 1 was used as Reagent a. Reagent a was stored at 30° C. for 1 month to prepare Reagent b. A mixture of 2.25 ml of the first reagent and 30 μl of 165 mM urea was preincubated at 37° C. for 5 minutes. Reagent a or b (0.75 ml) preincubated beforehand at 37° C. for 5 minutes was added thereto, and the mixture was subjected to reaction at 37° C. for 5 minutes. By measuring the decrease in the absorbance of the mixture at 340 nm per unit time, the urease activity was determined. The residual urease activity (%) was calculated from the urease activity of Reagent b and the urease activity of Reagent a according to the following equation.

Residual urease activity (%) =

$$\frac{\text{Urease activity of Reagent } b}{\text{Urease activity of Reagent } a} \times 100$$

The same procedure as described above was repeated except that triphenyl borate, tri-o-tolyl borate or boric acid was used instead of triethanolamine borate in the second reagent and the residual urease activity was calculated. As for triphenyl borate and tri-o-tolyl borate, these compounds were dissolved in N,N-dimethylformamide and then added to the second reagent, respectively.

Further, as a control experiment, the same procedure as above was repeated except that triethanolamine borate was excluded from the composition of the second reagent and the residual urease activity was calculated.

The results are shown in Table 3.

TABLE 3

| Concentration of additive (mM) | Residual urease activity (%) | | | |
|---|---|---|---|---|
| | boric acid | triethanol- amine borate | triphenyl borate | tri-o-tolyl borate |
| 0.01 | 20.6 | 39.6 | 35.6 | 40.1 |
| 0.05 | 31.2 | 70.8 | 65.2 | 68.3 |
| 0.10 | 35.4 | 76.8 | 70.3 | 72.4 |
| 0.20 | 40.5 | 82.3 | 75.6 | 80.8 |

TABLE 3-continued

| Concentration of additive (mM) | Residual urease activity (%) | | | |
|---|---|---|---|---|
| | boric acid | triethanol- amine borate | triphenyl borate | tri-o-tolyl borate |
| 0.40 | 45.6 | 91.2 | 80.4 | 83.6 |
| 0.80 | 52.6 | 92.6 | 86.2 | 90.6 |
| 1.60 | 75.8 | 97.4 | 92.3 | 93.4 |
| 2.50 | 80.6 | 98.3 | 94.6 | 96.6 |
| 0.00 (control group) | 11.2 | | | |

Table 3 reveals that the groups containing the organic boron compounds exhibit higher residual urease activity than the group containing boric acid at each concentration.

EXAMPLE 3

Assay reagent composition:

The following composition consisting of Reagent solutions 1 and 2 was prepared for quantitatively determining urea nitrogen.

| Reagent solution 1 | |
|---|---|
| Tris-hydrochloride buffer (pH 9.2) | 100 mM |
| α-KG | 1 mg/ml |
| NADPH | 0.3 mg/ml |
| Glutamate dehydrogenase | 20 U/ml |
| Reagent solution 2 | |
| Tris-hydrochloride buffer (pH 8.5) | 100 mM |
| α-KG | 4 mg/ml |
| Triethanolamine borate | 0.4 mM |
| Urease | 9 U/ml |

EXAMPLE 4

Assay reagent composition:

The following composition consisting of Reagent solutions 1 and 2 was prepared for quantitatively determining urea nitrogen.

| Reagent solution 1 | |
|---|---|
| Tris-hydrochloride buffer (pH 9.2) | 100 mM |
| α-KG | 1 mg/ml |
| NADPH | 6.3 mg/ml |
| Glutamate dehydrogenase | 20 U/ml |
| Reagent solution 2 | |
| Tris-hydrochloride buffer (pH 8.5) | 100 mM |
| α-KG | 4 mg/ml |
| Triphenyl borate | 0.4 mM |
| Urease | 9 U/ml |

EXAMPLE 5

Assay reagent composition:

The following composition consisting of Reagent solutions 1 and 2 was prepared for quantitatively determining urea nitrogen.

| Reagent solution 1 | |
|---|---|
| Tris-hydrochloride buffer (pH 9.2) | 100 mM |
| α-KG | 1 mg/ml |
| NADPH | 0.3 mg/ml |
| Glutamate dehydrogenase | 20 U/ml |
| Reagent solution 2 | |
| Tris-hydrochloride buffer (pH 8.5) | 100 mM |
| α-KG | 4 mg/ml |
| Tri-o-tolyl borate | 0.4 mM |
| Urease | 9 U/ml |

What is claimed is:

1. A method for quantitatively determining urea nitrogen in a sample, which comprises reacting urea nitrogen in the sample with urease in the presence of an organic boron compound which is selected from the group consisting of trialkyl borate, triaryl borate, trialkanolamine borate, triarylamine borate and tri-o-tolyl borate, determining ammonia formed by the reaction, and correlating the amount of ammonia to urea nitrogen.

2. The method according to claim 1, wherein the organic boron compound is selected from the group consisting of triethanolamine borate, triphenyl borate and tri-o-tolyl borate.

3. A method for preparing an assay reagent containing stabilized urease, which comprises adding to urease a stabilizing amount of an organic boron compound which is selected from the group consisting of trialkyl borate, triaryl borate, trialkanolamine borate, triarylamine borate and tri-o-tolyl borate.

4. A method according to claim 3, wherein $1 \times 10^{-10}$ to 1 mol organic boron compound is added per unit of urease.

5. The method according to claim 3 or 4, wherein the organic boron compound is selected from the group consisting of triethanolamine borate, triphenyl borate and tri-o-tolyl borate.

* * * * *